(12) United States Patent
Amitai et al.

(10) Patent No.: US 8,942,792 B2
(45) Date of Patent: Jan. 27, 2015

(54) ECG CALCULATION METHOD FOR USE IN GENERATING 12 LEAD ECG MEASUREMENTS FROM DEVICES THAT HAVE LESS THAN 10 ELECTRODES

(71) Applicants: Assaf Amitai, Paris (FR); David Amitai, Ramat Gan (IL)

(72) Inventors: Assaf Amitai, Paris (FR); David Amitai, Ramat Gan (IL)

(*) Notice: Subject to any disclaimer, the term of this patent is extended or adjusted under 35 U.S.C. 154(b) by 0 days.

(21) Appl. No.: 13/830,088

(22) Filed: Mar. 14, 2013

(65) Prior Publication Data

US 2014/0276153 A1    Sep. 18, 2014

(51) Int. Cl.
*A61B 5/0408*    (2006.01)
*A61B 5/0404*    (2006.01)
*A61B 5/0432*    (2006.01)
*A61B 5/0402*    (2006.01)
*A61B 5/00*    (2006.01)

(52) U.S. Cl.
CPC ........... *A61B 5/04028* (2013.01); *A61B 5/0404* (2013.01); *A61B 5/7278* (2013.01); *A61B 5/7475* (2013.01); *A61B 5/04085* (2013.01); *A61B 5/0432* (2013.01); *A61B 5/6893* (2013.01); *A61B 5/0006* (2013.01); *A61B 5/6828* (2013.01); *A61B 5/6825* (2013.01); *A61B 2560/0468* (2013.01)
USPC .......................................................... 600/509

(58) Field of Classification Search
USPC .................................. 600/509, 523
See application file for complete search history.

(56) References Cited

U.S. PATENT DOCUMENTS

2002/0143576 A1\* 10/2002 Nolvak et al. ..................... 705/2

\* cited by examiner

*Primary Examiner* — Carl H Layno
*Assistant Examiner* — Jon Eric C Morales
(74) *Attorney, Agent, or Firm* — Calvin B. Ward (57) ABSTRACT

A method for generating an ECG measurement associated with a point on a patient's body such as one of the precordial points is disclosed for use with an apparatus that cannot make contact with the leg and the point simultaneously. The method includes simultaneously recording a hand signal and a leg signal during a first time period. The hand signal is also measured during a second time period together with a chest signal corresponding to one of the precordial points. A signal representing the leg signal in the second time period is then computed from the first time period data. A reference signal is then generated from the hand signal and computed leg signal during the second time period. The reference signal is then combined with the chest signal to provide the corresponding precordial signal.

13 Claims, 4 Drawing Sheets

ECG CALCULATION METHOD FOR USE IN GENERATING 12 LEAD ECG MEASUREMENTS FROM DEVICES THAT HAVE LESS THAN 10 ELECTRODES

BACKGROUND OF THE INVENTION

Twelve lead ECG measurements are often used to analyze a patient's heart condition, and physicians are trained to interpret such measurements. In a clinical setting, the measurements are generated by attaching electrodes to the patient's hands, feet, and six locations on the patient's chest. Each chest measurement is made by measuring the potential as a function of time between one of the chest leads and the average of the potentials between the hands and one of the feet. This average is often referred to as "Wilson's Central-terminal". Unfortunately, generating such measurements in the field when the patient experiences symptoms that might correspond to a heart attack or other cardiovascular problem presents problems, since the conventional equipment and technicians are not usually available to connect the patient to the ECG device and make the measurements.

A number of portable ECG devices have been proposed to overcome the problem of making ECG measurements in the field. When a patient determines that the patient might be having a cardiac event, the patient uses the device to measure one or more ECG traces. If the device detects an anomaly in the traces, the results are sent to a physician for interpretation.

For example, U.S. Pat. No. 8,082,025 describes a handheld ECG device that measures the chest traces by placing the device against the corresponding locations of the patient's chest while holding the device in the patient's hands. The device is held such that one hand electrode on the device is in contact with the patient's left hand, and another hand electrode on the device is in contact with the patient's right hand. A chest measurement is then generated by measuring the potential between a third electrode that is in contact with the patient's chest and the average of the potentials measured by the hand electrodes. While the resultant ECG traces are a good approximation to the conventional chest traces, these traces can differ significantly from the conventional traces, and hence, present interpretation problems for physicians who are trained to interpret conventional ECG traces.

While an additional electrode could be attached between the device and the patient's foot or upper thigh to provide traces that more closely approximate the conventional ECG chest traces, the addition of such an electrode presents other problems. First, the electrode must be incorporated in the device in a manner that allows the electrode to be deployed and attached to the patient's leg by a wire. The wire and attachment mechanism are bulky, and hence, not easily incorporated in the device. If the wire and attached electrode are separate from the device, the electrode assembly is easily lost. The conventional attachment mechanisms utilize adhesively attached electrodes. These electrodes are not suitable for repeated use by a patient in the field; hence, some form of attachment that requires a band that holds the leg electrode against the patient's body is needed. This further increases the bulk of the portable device. In addition, the patient must be capable of attaching the electrode to the correct location. In the case of an elderly patient or someone with limited flexibility, attaching the leg electrode presents additional challenges.

SUMMARY OF THE INVENTION

The present invention includes a method for generating an ECG measurement associated with a point on a patient's body such as one of the precordial points. The ECG measurement depends on an average signal that includes signals from the left and right hands and one leg of a patient. The method of the present invention is useful when the measurement apparatus utilized for recording the signals, cannot make contact with the leg and the point in question simultaneously. The method includes simultaneously recording a hand signal and a leg signal during a first time period. In one aspect of the invention, the hand signal is a difference of the signals from the left and right hands, and the leg signal is a difference between one of the signals from the left or right hands and a signal from an electrode touching the patient's leg or lower abdomen.

The method further includes recording the hand signal during a second subsequent time period and computing a signal representing the leg signal in the second time period from the leg signal measured in the first time period and the hand signals measured in the first and second time periods. A computed reference signal for use in making precordial measurements is then generated from said leg and hand signals during said second time period.

DETAILED DESCRIPTION OF THE PREFERRED EMBODIMENTS OF THE INVENTION

Figure 1:
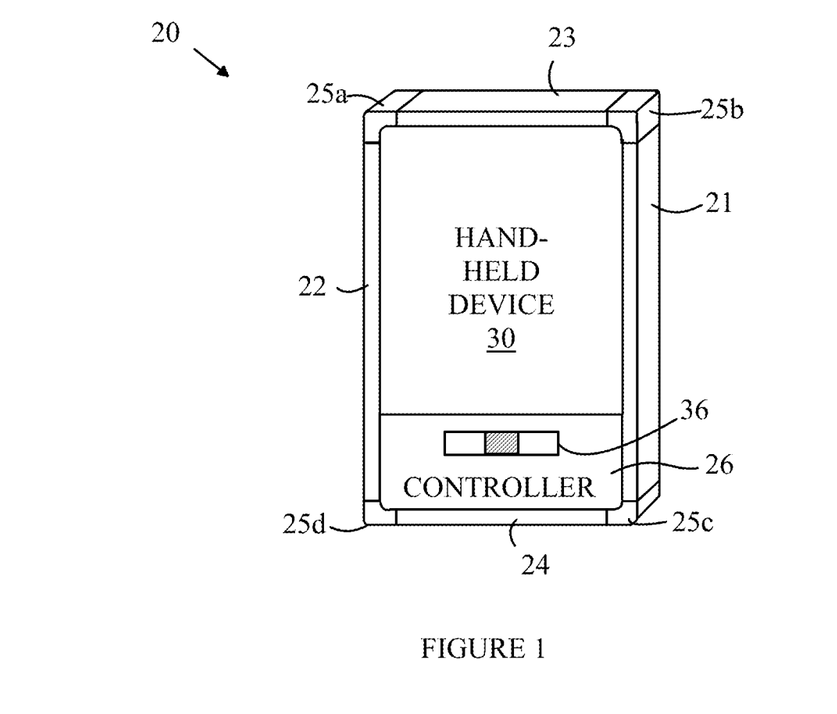
FIG. 1 illustrates one embodiment of an ECG data acquisition device according to the present invention.

The manner in which the present invention provides its advantages can be more easily understood with reference to the handheld device described in the above-identified US patent application. Refer now to FIG. 1, which illustrates one embodiment of an ECG data acquisition device that can utilize the present invention. ECG data acquisition device 20 may be viewed as comprising of two components. The first component is a handheld device 30 such as a cellular telephone or personal data assistant (PDA) that is used to process the measurements and, optionally, forward the measurements to a remote location for evaluation. The second component, referred to as the electrode component, is a set of electrodes and a controller that are attached to the outside of handheld device 30 or incorporated in a single device. The electrodes are shown at 21-24, respectively, and are separated from one another electrically by insulating the regions shown at 25a-25d.

The manner in which ECG data acquisition device 20 is used to generate a 12 lead ECG will now be explained in more detail. A conventional 12 lead ECG involves the placement of ten electrodes at designated places on the patient's body. The signals from these ten electrodes are then processed to generate 12 graphs of voltage as a function of time that are called the ECG chart or diagram. In the conventional ECG measurements, four electrodes are attached to the patient's limbs, typically on the wrists and ankles. These electrodes are referred to as the standard lead electrodes. The remaining six electrodes are attached to specific points on the patient's chest. These electrodes are referred to as the precordial lead electrodes.

A 12 trace ECG diagram is obtained using ECG data acquisition device 20 by holding the ECG data acquisition device with both hands and pressing electrode 24 against the appropriate place on the patient's body. The placement of electrode 24 depends on which of the traces in the ECG diagram is being measured. In one embodiment, electrodes 21 and 22 are held in the right hand with the thumb on electrode 21 and the right index finger on electrode 22. The left index finger or any part of the left palm is held on electrode 23. It should be noted that electrode 22 can be touched with other fingers of the right hand besides the index finger. Electrode 21 can also be touched with other fingers or part of the right hand. The type of measurement being performed can be communicated to controller 26 through mode switch 36, which has a plurality of predetermined positions. For the standard lead measurements, mode switch 36 is set to a first position, and electrode 24 is placed against any point of the left leg or the lower left abdomen. For the precordial measurements, mode switch 36 is set to a second position, and electrode 24 is placed sequentially at each of the precordial positions on the patient's chest.

As noted above, the four conventional electrodes are placed on the left and right wrists and the left and right ankles. In ECG data acquisition device 20, these measurements are provided by using the electrode in contact with the right index finger, i.e., electrode 22, in place of the conventional electrode in contact with the right wrist, the electrode in contact with the right thumb, i.e., electrode 21 in place of the conventional electrode in contact with the right ankle, the electrode in contact with the left index finger, i.e., electrode 23, in place of the conventional electrode in contact with the left wrist, and the electrode in contact with the left leg, i.e., electrode 24 in place of the conventional electrode in contact with the left ankle.

Denote the potential from electrode 22 by $\Phi_r$ (right hand), the potential from electrode 23 by $\Phi_l$ (left hand), and the potential from electrode 24 $\Phi_f$ (left leg). In practice, signals are always measured between pairs of electrodes to reduce errors created by common mode noise. The first three standard lead traces are given by $$I = \Phi_l - \Phi_r,$$

$$II = \Phi_f - \Phi_r, \text{ and}$$

$$III = \Phi_f - \Phi_l = II - I \quad (1)$$

These traces are each functions of time. In the following discussion, the lead I signal as a function of time will be referred to as the hand signal. The lead II signal as a function of time will be referred to as the leg signal.

Three additional traces are generated by utilizing weighted sums and differences of the lead I and II signals, namely $$aVR = \Phi_r - (\Phi_l + \Phi_f)/2 = -(I+II)/2,$$

$$aVL = \Phi_l - (\Phi_r + \Phi_f)/2 = I - II/2, \text{ and}$$

$$aVF = \Phi_f - (\Phi_r + \Phi_l)/2 = II - I/2. \quad (2)$$

The six traces described above are measured as a function of time and are commonly known as the standard leads or standard lead traces. The measurements of the difference potentials and the computation of the second three weighted sums can be performed in controller 26, the handheld device or at an external facility connected to the handheld device.

The remaining six traces of the conventional 12 lead ECG are the precordial traces (V1-V6). In the conventional precordial measurements, each trace is generated by forming the average of the potentials from the right and left wrists and the left leg (this averaged potential is known as Wilson's Central-Terminal $\Phi_{CT}$) and then measuring the difference between $\Phi_{CT}$ and a potential, $\Phi_i$, detected by an electrode at a corresponding point on the patient's chest. A different predetermined point on the chest is used for each of the six traces:

$$V_i = \Phi_i - (\Phi_l + \Phi_f + \Phi_r)/3 = \Phi_i - \Phi_{CT}. \quad (3)$$

The average signal from the hands and leg is often referred to as the "C-terminal". It should be noted that a C-terminal signal can be generated from other locations on the three extremities in question. For example, the potentials corresponding to the leg can be measured at the foot, angle, or upper thigh or lower abdomen. Similarly, the potentials corresponding to the "hands" can be measured any place between one of the fingers and the shoulder.

The handheld device discussed above cannot simultaneously measure the potential at the chest, $\Phi_i$, and the left leg, $\Phi_f$. Hence, some approximation for $\Phi_{CT}$ must be utilized. In the above-described US patent application, the average of $\Phi_r + \Phi_l$ is utilized to approximate $\Phi_{CT}$. In this case, the precordial traces are approximated by $$\tilde{V}_i = \Phi_i - \frac{\Phi_r + \Phi_l}{2}. \quad (4)$$

However, in some cases, corrections to the approximated precordial signal that compensate for the missing leg potential may be desirable to provide precordial traces that more closely match the traces that would be obtained with a conventional ECG measurement apparatus, since physicians are trained to interpret the standard traces.

As noted above, all of the signals are functions of time. That is $\Phi_{CT} = \Phi_{CT}(t)$, $\Phi_r = \Phi_r(t)$, and so on. Similarly, the lead I and lead II signals as defined above will be denoted by the functions of time, $S_I(t)$ and $S_{II}(t)$, respectively. These signals will also be referred to as the hand and leg signals, respectively, in the following discussion; however, as noted above, $S_{II}(t)$ could be measured at a place on the lower abdomen. Accordingly, the term leg signal includes the case in which the $S_{II}(t)$ is measured on the lower abdomen. To obtain a better approximation for $\Phi_{CT}(t)$ than the one provided in Equation 4 as the average of the hand signals, an approximation for $\Phi_r(t)$ is needed during the time period in which the third electrode is in contact with the chest. In the present invention, this approximation is generated from the previously measured leg signal, $S_{II}(t)$, that was observed during the standard lead trace measurements.

To simplify the discussion, the time period during the standard lead measurements are recorded by the time interval $[0, T_1]$. The precordial signal is measured during a later time interval $[T_2, T_3]$. In terms of this nomenclature, the problem can be stated as follows. Given $S_I(t)$ for t in $[0, T_1]$, determine an approximation for $S_{II}(t)$ for t in $[T_2, T_3]$.

The present invention utilizes the observation that there is a relationship between $S_I(t)$ and $S_{II}(t)$ measured during the different time periods. That is, there is a relationship between the signals from the hand signal and the leg signal. The hand signal is measured during both time periods. In the present invention, the relationship between the hand signals in the two time periods is utilized to transform the leg signal during the first time period to an approximation of the leg signal that would have been measured in the second time interval. This strategy depends on the assumption that the leg signal during the second time period is related to the leg signal during the first time period in a manner that can be determined by examining the changes in the hand signal between the first time period and the second time period. The manner in which this assumption is verified during the actual measurements will be discussed in more detail below.

Figure 2A:
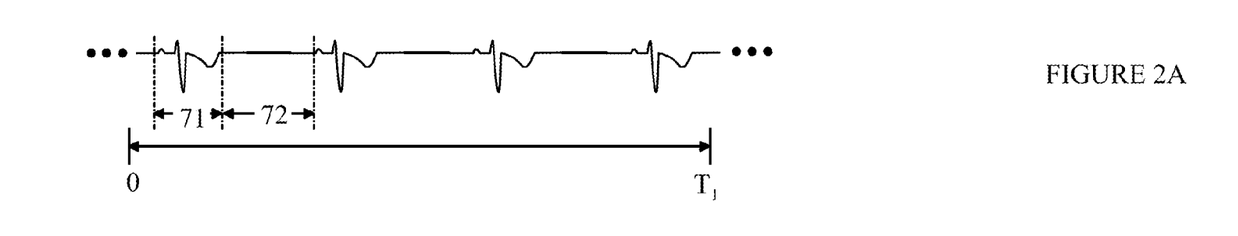
FIGS. 2A-2C illustrate two lead signals measured at different times.
Figure 2B:
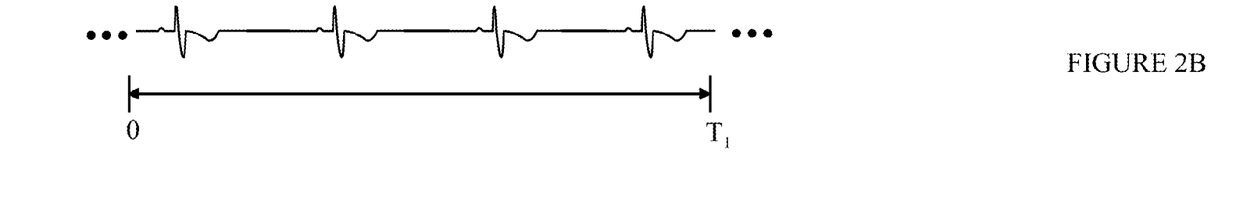

Refer now to FIG. 2A, which illustrates a typical leg signal (lead II) as a function of time, i.e., $S_{II}(t)$, during the first time interval. The trace can be viewed as complex 71 separated by time intervals 72 of relative electrical inactivity. The complexes are the electrical signals generated by the heart during a heartbeat. Refer now to FIG. 2B, which illustrates the hand signal (lead I), i.e., $S_I(t)$ taken during the same time interval. The complexes in $S_I(t)$ are synchronized with those in $S_{II}(t)$.

Figure 2C:
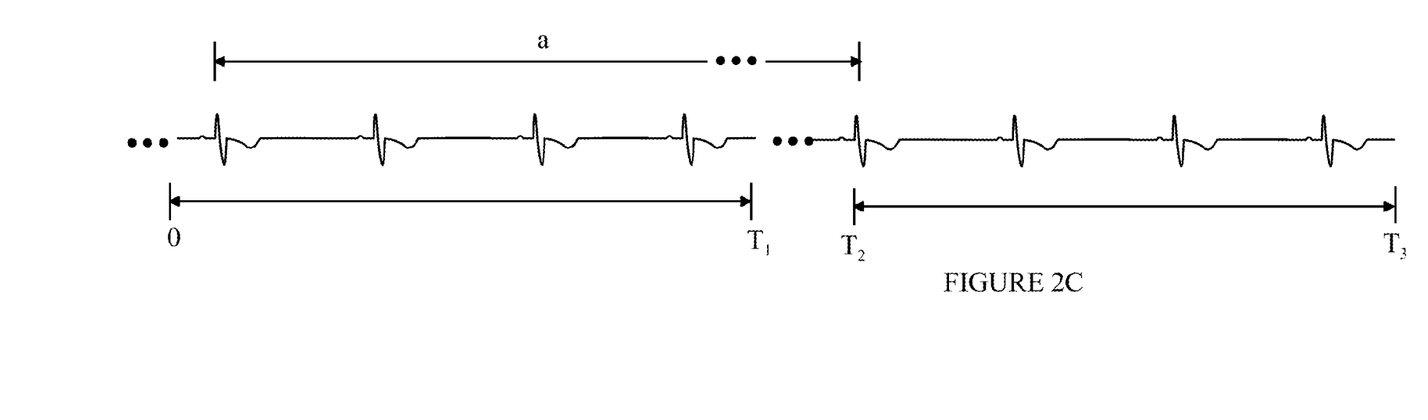

Consider the simple case in which the signals in the second time interval are the same as those in the first time interval. That is, the shapes of the complexes and the spacing of the complexes remains the same, and hence, the signal in the second time interval is the same as that in the first time interval shifted in time. That is, there is a constant, "a", such that $S_I(t)=S_I(t-a)$ for t in $[T_2, T_3]$ and (t-a) in $[0, T_1]$. In this simple case, the constant, a, can be determined by comparing the values of SAO in the two time intervals as shown in FIG. 2C. Given this value of the constant a, and that the leg signal during the second time interval is just a shift of the lead leg signal from the first time interval. That is, the approximation to the leg signal in the second time interval is then given by $S'_{II}(t)=S_{II}(t-a)$ for t in $[T_2, T_3]$.

This simple example is provided to illustrate the basic principle of the present invention; however, in practice, the traces are not the same over both time intervals. For example, the heart rate can vary significantly between the two time intervals. The shape of the complexes can likewise be different. Hence, a more complicated time transformation is, in general, needed.

To simplify the following discussion, denote the signals measured during the standard leads measurement at a first time interval $[0, T_1]$, by $S_{I,1}(t)$ and $S_{II,1}(t)$, given by $$S_{I,1}(t)=\Phi_l(t)-\Phi_r(t), \quad (5)$$

$$S_{II,1}(t)=\Phi_f(t)-\Phi_r(t), \quad (6)$$

where the Roman number represents the lead trace and the Arabic indicates the time interval.

Similarly, denote the signals measured during one of the precordial trace recordings at time interval, $[T_2, T_3]$, between the two hands by $S_{I,2}(t)$ and between the i-th precordial location and the right hand:

$$S_{i,2}(t)=\Phi_i(t)-\Phi_r(t) \quad (7)$$

This signal will be referred to as a chest signal in the following discussion. There are six such chest signals, each chest signal corresponding to a different location on the patient's chest. As noted above, the present invention is based on the observation that the leg signal measured in the first time interval can be used to provide an approximation to the leg signal that would have been measured in this new time interval.

In one aspect of the present invention, a mapping function, $f(t, a_1, a_2, \ldots)$ is defined for t in the second interval, $[T_2, T_3]$, such that $f(t, a_1, a_2, \ldots)$ is a time in the first time interval, $[0, T_1]$ that corresponds to time t in the second time interval. Ideally, the values of the parameters, $a_1, a_2, \ldots$ are chosen such that the hand signals measured at each time in the second time interval match the hand signals measured in the first time interval at a time given by $f(t, a_1, a_2, \ldots)$. The function $f(t, a_1, a_2, \ldots)$ will be referred to as the time transformation function in the following discussion. In practice, the parameters are chosen such that the differences in the hand signals in the two time intervals are minimized. For example, $a_1, a_2, \ldots$ can be chosen to minimize an error function $E(a_1, a_2, \ldots)$ given by $$E(a_1,a_2,\ldots)=\int_{T_2}^{T_3}[S_{I,2}(t)-S_{I,1}(f(t,a_1,a_2,\ldots))]^2 dt. \quad (8)$$

Given this choice of $a_1, a_2, \ldots$, the leg signal for t in the second interval is approximated by $$S'_{II,2}(t)=S_{II,1}(f(t,a_1,a_2,\ldots)). \quad (9)$$

The precordial traces are then defined to be $$V_i(t)=S_{i,2}(t)-\tfrac{1}{3}(S'_{II,2}(t)+S_{I,2}(t)) \quad (10)$$

The above-described procedure assumes that the function $f(t, a_1, a_2, \ldots)$ is known to within n parameters, $a_1, a_2, \ldots a_n$. As noted above, the simplest form of this function would be $$f(t)=a_1+t, \quad (11)$$

which corresponds to the case in which the hand and leg signals remain constant between the measurement of the standard lead traces and the precordial lead traces. That is, the signal $S_{II,2}(t)$ is just the signal $S_{II,1}(t)$ shifted in time, and the signal $S_{I,2}(t)$ is just the signal $S_{I,1}(t)$. This case assumes that the heart rate remains constant between measurements.

If the heart rate changes between measurements, the time intervals 71 and 72 shown in FIG. 2A will change. Consider the case in which the heart speeds up during the second time interval. Then the length of time intervals 71 and 72 will be reduced during the second time interval relative to the length of the intervals during the first time interval. The amount by which the time intervals decrease will, in general, be different for the complex region and the region between the complexes. If only a change in rate is present, $$f(t) = \begin{cases} a_1 t + b_1 & \text{for } 0 \le t \le T_{71}, \\ a_2 t + b_2 & \text{for } T_{71} < t \le T_{72}, \end{cases} \quad (12)$$

where $T_{71}$ and $T_{72}$ are times within time intervals 71 and 72 respectively, $b_1$ is the time shift between the first time interval and the second, $a_1$ represents the ratio of heart rate between the two time intervals within the complex, $a_2$ represents the ratio of heart rate between the two time intervals within the inter-complexes intervals and $b_2$ is the time shift between them.

Figure 3:
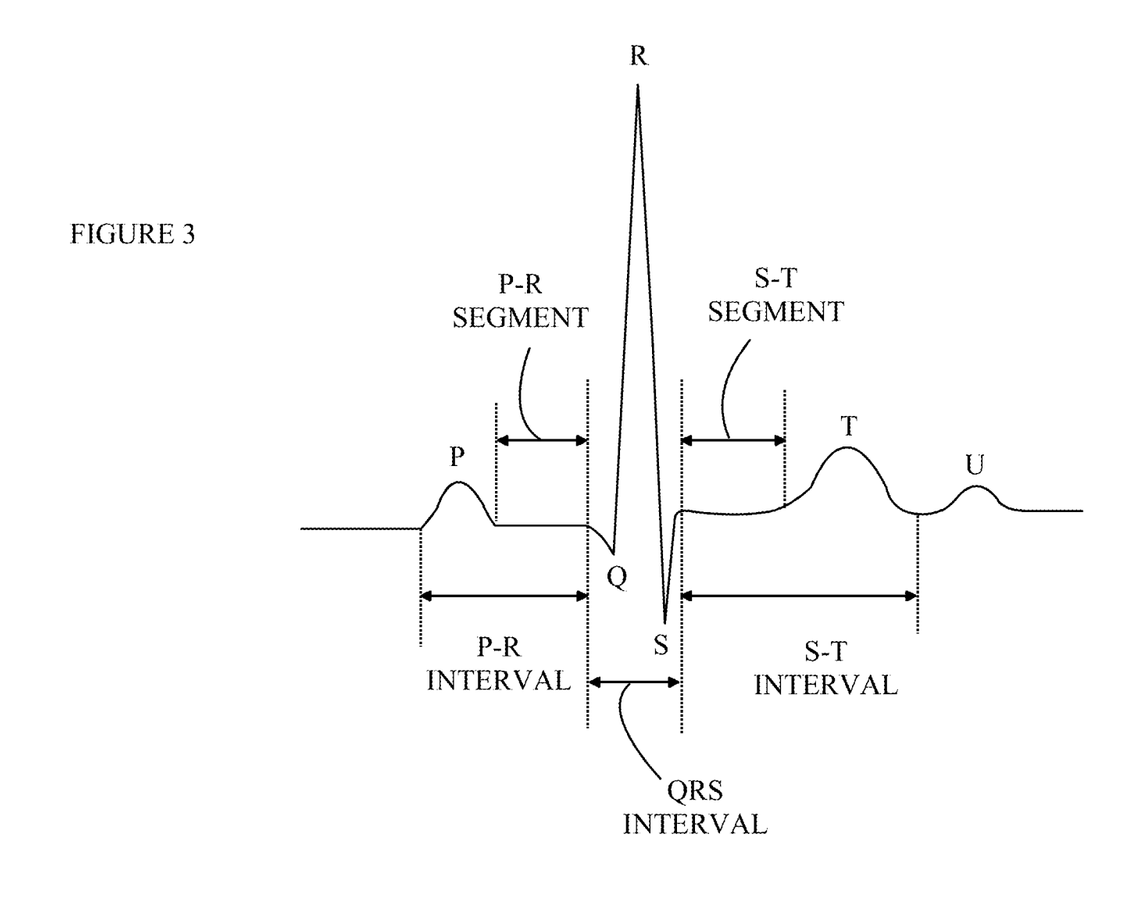
FIG. 3 illustrates an ECG complex and the conventional elements identified within that complex.

The use of separate time transformations on different intervals of the measured signals can be generalized to take into account the known intervals in the complexes. Refer now to FIG. 3, which illustrates an ECG complex and the conventional elements identified with that complex. The individual intervals within the complex depend on the heart rate. In one aspect of the invention, the model discussed above with reference to Equation (12) is expanded to include a separate time transformation for each of the intervals or segments shown in FIG. 3. The parameters of the time transformation are determined by a comparison of the various intervals and segments between the measured lead I signals $S_{I,1}(t)$ and $S_{I,2}(t)$ in the first and second time intervals, respectively.

If the shape changes within the complex intervals in a manner that cannot be accommodated by a simple time contraction or expansion, a more complicated transformation can be utilized within the complex time intervals. For example, a more complicated time transformation function, which takes into account changes in the heart rate can be constructed from a Gaussian and a linear function of the form $$f(t) = a_0 + a_3 \mathrm{Exp}\left[\frac{-(t-a_1)^2}{2a_2}\right] + a_4 t, \quad (13)$$

where the parameter $a_0$ represents the time difference between the specific complex intervals, $a_1$ determines the center of the region that undergoes the transformation, $a_2$ determines the width of the pulse region undergoing the transformation, which will be approximately the time length of the modified region, $a_3$ determines the amount of local contraction and shifting in time the signal undergoes and $a_4$ reflects a change in the total length of the signal. While this form of f(t) uses a single Gaussian, embodiments in which more than one Gaussian are determined can be used.

To further improve the approximation for $S_{II,2}(t)$ during the precordial measurements, the standard lead measurements can be repeated between each measurement of a precordial point, and the constants of the time transformation function recomputed. That is, a first standard lead measurement with electrode 24 against the leg is made to provide the signals $S_{I,1}(t)$ and $S_{II,1}(t)$. A precordial measurement is then made by placing electrode 24 against the corresponding precordial point on the patient's chest. The calibration constants are then determined to provide the approximation $S'_{II,2}(t)$ that is used with $S_{I,2}(t)$ and $S_{I,2}(t)$ to provide the precordial trace in question. The process is then repeated for each of the remaining precordial points.

The above-described procedure depends on an approximation to the changes in the leg signal between the standard lead measurements and precordial measurements being adequately represented by the time transformation discussed above. Accordingly, in one aspect of the invention, the validity of this approximation is tested to determine if the model on which the approximation is based is valid during the time periods in question. There are a number of methods that could be utilized to test the validity of the approximation. In one aspect of the invention, the minimum value $E(a_1, a_2, \ldots)$ obtained in the fitting of the parameters to the hand data is compared to a predetermined threshold value. If the value is greater than that threshold value, the approximation is deemed to be invalid, and the precordial measurement is repeated until the error limit is less than the threshold value.

In another aspect of the invention, the recorded signal $S_{II,1}(t)$ is compared by utilizing another time mapping function. At the end of the second standard lead measurement, signals $S_{I,3}(t)$ and $S_{II,3}(t)$ will have been recorded. A time mapping function, f'(t) can be computed from $S_{I,2}(t)$ utilizing the previously measured signal $S_{I,2}(t)$ using the method described above. The function f'(t) maps times in the first time period to times in the third time period. If the lead II has remained stable during the third time period, $S_{II,3}(t)$ should be equal to $S_{II,1}(f'(t))$. In one aspect of the invention, an error function $E_{II}$ can be computed. If $E_{II}$ is greater than some predetermined error limit, the lead II signal is not sufficiently constant to ensure that the approximation is valid. In this case, the precordial measurement can be repeated until the error is less than the limit. In one aspect of the invention, the error function is computed according to $$E_{II}(a_1, a_2, \ldots) = \int_{T_4}^{T_5} [S_{II,3}(t) - S_{II,1}(f(t, a_1, a_2, \ldots))]^2 dt \quad (14)$$

At the end of the precordial measurement process, at least six additional standard lead measurements will have been made. If the standard lead traces vary significantly from measurement to measurement, the apparatus can also report to the user that the method is not working satisfactorily. In addition, such variations may also be diagnostic of an underlying unstable heart condition.

The above-described measurement procedures also depend on the time intervals chosen to compute the transformation function that maps the precordial measurement time interval into the standard lead time interval. Typically, the standard lead and precordial signals are recorded for a few seconds. Each recording contains data on a number of complexes. Successful diagnosis requires the analysis of a small number of representative complexes. Abnormal complexes appear spontaneously in the normal cardiac pattern. Such abnormalities can interfere with the above-described method, since the hand signals in the two time periods will not correlate well if one of the time periods contains a spontaneous abnormality.

In one aspect of the invention, the time periods are chosen to reduce the effects of such spontaneous abnormalities. Each time period used in the computation is selected to contain a predetermined number of complexes (i.e., heartbeats). The process starts by selecting a predetermined number of complexes from the standard lead measurement. The goal is to find the best match for these measurements in the corresponding precordial measurement period. Hence, the second time interval is chosen to have the same number of complexes and can be viewed as starting at the beginning of a particular complex. The error function, $E(a_1, a_2, \ldots)$ is then computed for each time period in the precordial measurement period as a function of the starting complex. The starting complex that provides the lowest value for $E(a_1, a_2, \ldots)$ is then used to define the time period for the precordial measurements. This procedure assumes that the starting time for the complexes in the standard lead measurement interval remains the same for each choice of time period in the precordial measurement interval. However, embodiments in which the minimum value of $E(a_1, a_2, \ldots)$ is computed for each possible starting complex in each of the time periods can also be utilized to further improve the measurements.

After applying the time transformation function, the two lead I signals may still exhibit differences in amplitude. Although these do not appear significant, they may be important when calculating the correct $S'_{II,2}(t)$. The voltage value of leads I and II are correlated as both share the right hand potential information and they are different representations of the same cardiac activity. We use this correlation to find the approximated amplitude value of the $S'_{II,2}(t)$. To find the proper amplitude transformation that would give us the approximation for the amplitude at specific region of the signal, a scaling factor, h(t), is determined such that $E_{Amp}$ given by $$E_{Amp}(a_1, a_2, \ldots) = \int_{T_2}^{T_3} [S_{I,2}(t) - S_{I,1}(f)]^2 dt \quad (15)$$

is minimized. The simplest form of h(t) is a constant:

$$h = a_1. \quad (16)$$

Figure 4:
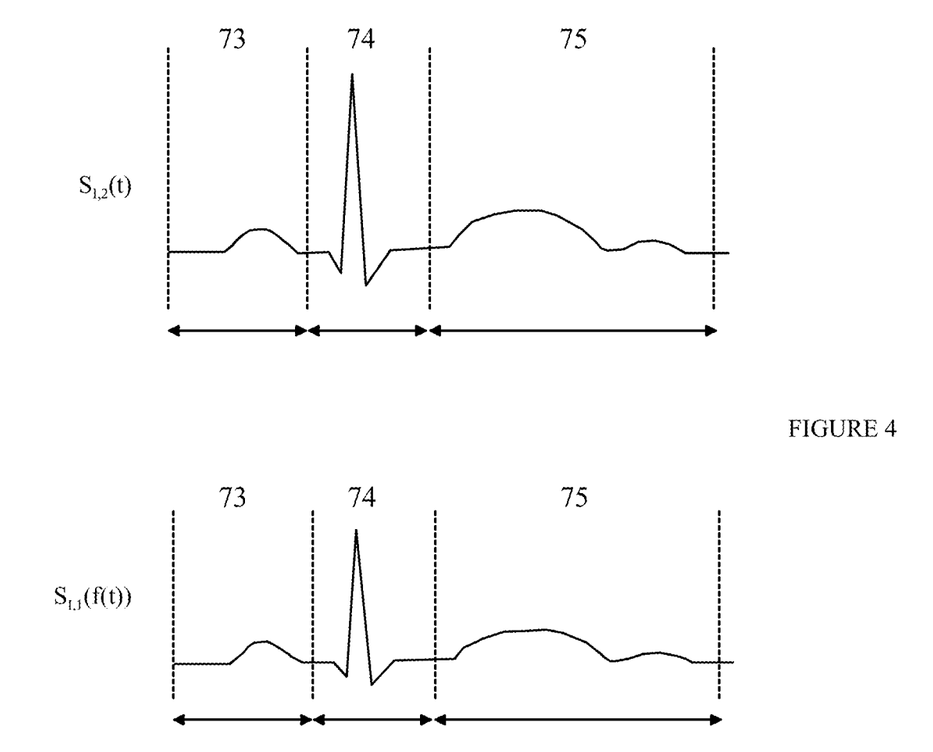
FIG. 4 illustrates a number of time periods that are useful in adjusting an amplitude correction factor.

However, higher order functions could be utilized. For example, the differences in the amplitude between the signals $S_{I,1}(t)$ and $S_{I,2}(t)$ may depend on the position along the complex, where the amplitude difference in the P wave is different from that of the QRS wave. Refer to FIG. 4, which illustrates one complex of a signal $S_{I,2}(t)$ and the time-transformed signal $S_{I,1}(f(t))$. These signals are decomposed into three intervals: 73, 74, 75. The value of amplitude transformation function h(t) is a constant within each interval, i.e., $$h(t) = \begin{cases} a_1 & \text{for } 0 \leq t \leq T_{73}, \\ a_2 & \text{for } T_{73} < t \leq T_{74}, \\ a_3 & \text{for } T_{74} < t \leq T_{75}. \end{cases} \quad (17)$$

The values of the constants, a1, a2, and a3, are determined by minimizing $E_{amp}$. The number of free parameters used to determine h(t) is restricted by the number of samples in the signals. After finding the best amplitude transformation function h(t), the amplitude correction is applied to $S'_{II,2}(t)$ to get a better approximation for the lead II signal as it would have been measured at the second time period.

The above-described embodiments of the present invention have been discussed in terms of the specific apparatus shown in FIG. 1. However, the method of the present invention can be applied in any situation in which multiple signals are needed to reference a chest measurement and only signals from two of the three points are available to generate the reference signal during the chest measurement. For example, systems for generating 12 lead ECG traces from a device that has three electrodes on the bottom surface of a probe that is placed against the chest and two electrodes that are contacted on the top surface of the device with a finger from each hand have been suggested. The present invention could be utilized to provide an improved reference signal to replace the signals from the fingers by first placing the device against the leg to provide a leg signal that is then used to construct a reference signal when the chest signals are measured using only the fingers.

In the above-described embodiments, it is assumed that the apparatus that records the potentials at the various locations on the patient's body also performs the fitting operation to arrive at the approximated signals. However, embodiments in which the signals from the electrodes are recorded by the apparatus and then sent to a remote location for analysis could also be constructed. Such remote processing embodiments are particularly useful in cases in which the computational capacity of the data acquisition device is limited. The remote device could be accessed over the internet or be a local computer such as a smartphone or PDA that has more computational capacity than the device making the measurements.

In the above-described embodiments, the signals are generated by electrodes that contact fingers on the hands and the thigh of the patient. However, embodiments that make contact at other locations on the patient's body could also be used. Accordingly, contact with a hand is defined to include contact with any portion of the hand attached to that hand including the fingers, hands, forearm or upper arm. Similarly, contact with a leg is defined to include contact with any point between the hip and the ends of the toes on that leg.

In the above-described embodiments, right hand contact is used as the reference against which the hand, leg, and chest signals are measured. However, the left hand could likewise be used as the reference signal against which the other signals are measured.

The above-described embodiments of the present invention have been provided to illustrate various aspects of the invention. However, it is to be understood that different aspects of the present invention that are shown in different specific embodiments can be combined to provide other embodiments of the present invention. In addition, various modifications to the present invention will become apparent to those skilled in the art from the foregoing description and accompanying drawings. Accordingly, the present invention is to be limited solely by the scope of the following claims.

What is claimed is:

1. A method for generating an ECG measurement that depends on an average signal that includes signals from the left and right hands and one leg of a patient, said method comprising:
    simultaneously recording a hand signal and a leg signal during a first time period, said hand signal comprising a difference of said signals from said left and right hands;
    recording said hand signal during a second subsequent time period;
    computing a signal representing said leg signal in said second time period from said leg signal during said first time period by comparing a function of said hand signals during said second time period with said function of said hand signals during said first time period; and
    generating a computed reference signal representing said leg and hand signals during said second time period.

2. The method of claim 1 further comprising
    recording a chest signal during said second time period, said chest signal comprising a difference between a signal measured on a precordial measurement point on said patient's chest and one of said left and right hands; and
    generating a precordial signal comprising a difference of said computed reference signal and chest signal.

3. The method of claim 1 wherein generating said computed reference signal comprises
    combining said computed signal representing said leg signal in said second time period with said hand signal measured in said second time period to provide an averaged signal during said second time period.

4. The method of claim 1 wherein computing said signal representing said leg signal in said second time period comprises:
    determining a time transformation that maps each time in said second time period to a time in said first time period by fitting said hand signals in said first time period to a corresponding hand signal in said second time period; and
    for each time in said second time period, setting said leg signal equal to said leg signal in said first time period at a time determined by said time transformation.

5. The method of claim 4 wherein said leg signal in said second time period is scaled by a factor that depends on said hand signals during said first and second time periods.

6. The method of claim 5 wherein said factor is time dependent.

7. The method of claim 4 wherein said time transformation comprises a plurality of constants that are determined by said fitting.

8. The method of claim 4 wherein said fitting generates an error estimate and wherein said leg signal is only used if said error estimate is less than a predetermined threshold.

9. The method of claim 8 wherein said first and second time periods are chosen to minimize said error estimate.

10. A method for generating a precordial ECG measurement with a probe having first, second, and third electrodes on an outer surface of a housing, said method comprising:
    simultaneously contacting said patient's left hand with said first electrode, said patient's right hand with said second electrode, and one of said patient's legs with said third electrode;
    measuring signals between said first, second, and third electrodes during a first time period and generating a hand signal and a leg signal in said first time period;
    placing said third electrode against a predetermined point on said patient's chest while contacting said first and second electrodes with said left and right hands, respectively;
    measuring signals between said first, second, and third electrodes during a second time period to provide a chest signal and a hand signal during a second time period;
    computing an approximate leg signal in said second time period from said measured hand and leg signals during said first time period by comparing said hand signal in said second time period with said hand signal during said first time period; and computing the difference between said chest signal and a weighted sum of said approximate leg signal and said hand signal in said second time period to provide said chest measurement.

11. The method of claim 10 further comprising:
placing said third electrode against said patient's leg while contacting said first and second electrodes with said patients left and right hands, respectively;
measuring signals from said first, second, and third electrodes during a third time period to provide a hand signal and a leg signal during said third time period; and
comparing said leg signal during said third time period with said leg signal during said first time period.

12. The method of claim 11 wherein said comparing of said leg signals comprises:
determining a time transformation that maps each time in said third time period to a time in said first time period by fitting said hand signal in said first time period to a said hand signal in said third time period; and
for each time in said third time period, comparing said leg signal in said first time period, to said leg signal in said third time period at a time determined by said time transformation.

13. The method of claim 11 further comprising notifying said patient if said comparison indicates that said leg signals in said first and third time periods differ by more than a predetermined amount.

* * * * *